United States Patent
Shreve et al.

(10) Patent No.: US 9,289,768 B2
(45) Date of Patent: Mar. 22, 2016

(54) APPARATUS FOR REDUCING VARIATION IN SAMPLE TEMPERATURES IN A LIQUID CHROMATOGRAPHY SYSTEM

(75) Inventors: Joshua A. Shreve, Franklin, MA (US); James E. Usowicz, Webster, MA (US); Miguel Soares, Norton, MA (US)

(73) Assignee: Waters Technologies Corporation, Milford, MA (US)

( * ) Notice: Subject to any disclaimer, the term of this patent is extended or adjusted under 35 U.S.C. 154(b) by 434 days.

(21) Appl. No.: 13/520,189

(22) PCT Filed: Jan. 11, 2011

(86) PCT No.: PCT/US2011/020735
§ 371 (c)(1),
(2), (4) Date: Jul. 2, 2012

(87) PCT Pub. No.: WO2012/096649
PCT Pub. Date: Jul. 19, 2012

(65) Prior Publication Data
US 2013/0019695 A1    Jan. 24, 2013

Related U.S. Application Data

(60) Provisional application No. 61/293,832, filed on Jan. 11, 2010.

(51) Int. Cl.
*G01N 21/13* (2006.01)
*B01L 7/02* (2006.01)
(Continued)

(52) U.S. Cl.
CPC ........... *B01L 7/02* (2013.01); *B01L 2300/0829* (2013.01); *B01L 2300/1838* (2013.01);
(Continued)

(58) Field of Classification Search
CPC ....... G01N 30/02; G01N 30/90; G01N 35/04; G01N 35/025; G01N 35/1074; G01N 2030/025; G01N 30/24; G01N 30/54; B01L 2300/0829; B01L 3/50851; B01L 2300/1822
See application file for complete search history.

(56) References Cited

U.S. PATENT DOCUMENTS 3,841,059 A    10/1974   McCabe
4,335,620 A     6/1982   Adams
(Continued)

FOREIGN PATENT DOCUMENTS

WO        0067872 A2     11/2000

OTHER PUBLICATIONS

International Search Report and Written Opinion for counterpart international patent application No. PCT/US2011/020735 dated Mar. 11, 2011; 7 pages.
(Continued)

*Primary Examiner* — David A Rogers
(74) *Attorney, Agent, or Firm* — Schmeiser, Olsen & Watts LLP; William G Guerin

(57) ABSTRACT

Described is an apparatus for reducing a temperature variation of a liquid chromatography sample. A tray drive using at least one of linear or rotational motion moves a sample tray along a path inside a sample compartment of the liquid chromatography system. A control module coordinates the movement of the sample tray by the tray drive and the movement of a sample needle by a needle drive so that any sample in the sample tray can be injected into the mobile phase of the system during a sample load operation. The tray drive is also used to move the sample tray along the path during a temperature averaging period when no loading occurs. Differences in sample temperatures due to variations in the air temperature at different locations inside the sample compartment are reduced, leading to more accurate and repeatable chromatographic measurement results.

14 Claims, 2 Drawing Sheets

(51) Int. Cl.
*G01N 30/72* (2006.01)
*G01N 35/00* (2006.01)
*G01N 35/02* (2006.01)

(52) U.S. Cl.
CPC .......... *G01N30/7233* (2013.01); *G01N 35/028* (2013.01); *G01N 2035/00356* (2013.01); *G01N 2035/00386* (2013.01)

(56) References Cited

U.S. PATENT DOCUMENTS

| | | | | |
|---|---|---|---|---|
| 5,207,987 | A * | 5/1993 | Kureshy | B01L 7/00 219/388 |
| 5,314,825 | A * | 5/1994 | Weyrauch et al. | 436/43 |
| 5,585,068 | A * | 12/1996 | Panetz et al. | 422/64 |
| 6,207,031 | B1 * | 3/2001 | Adourian et al. | 204/451 |
| 6,352,861 | B1 * | 3/2002 | Copeland et al. | 436/46 |
| 6,881,579 | B2 * | 4/2005 | Hilson et al. | 436/47 |
| 6,945,129 | B2 * | 9/2005 | Escal | 73/864.24 |
| 8,806,965 | B2 * | 8/2014 | Sato et al. | 73/863.11 |
| 2002/0122745 | A1 | 9/2002 | Takase et al. | |
| 2003/0224395 | A1 | 12/2003 | Javanovich et al. | |
| 2004/0009099 | A1 | 1/2004 | Bizet et al. | |
| 2006/0266719 | A1 * | 11/2006 | Knight et al. | 211/74 |
| 2007/0154895 | A1 * | 7/2007 | Spaid et al. | 435/6 |
| 2008/0145282 | A1 | 6/2008 | Efimov et al. | |
| 2008/0314812 | A1 * | 12/2008 | Kareh | B01D 15/24 210/198.2 |
| 2009/0068074 | A1 * | 3/2009 | Ammann et al. | 422/307 |
| 2009/0130749 | A1 * | 5/2009 | Ammann et al. | 435/303.3 |
| 2009/0220379 | A1 * | 9/2009 | Wakamiya et al. | 422/65 |
| 2010/0240063 | A1 * | 9/2010 | Hayes et al. | 435/6 |
| 2011/0147610 | A1 * | 6/2011 | Macioszek et al. | 250/429 |

OTHER PUBLICATIONS

Extended Search Report in counterpart European Patent Application No. 11855267.8, mailed on Jun. 15, 2015; 6 pages.

* cited by examiner

US 9,289,768 B2

APPARATUS FOR REDUCING VARIATION IN SAMPLE TEMPERATURES IN A LIQUID CHROMATOGRAPHY SYSTEM

RELATED APPLICATION

This application claims the benefit of the earlier filing date of U.S. Provisional Patent Application Ser. No. 61/293,832, filed Jan. 11, 2010 and titled "Apparatus for Reducing Variation in Sample Temperatures in a Liquid Chromatography System," the entirety of which is incorporated herein by reference.

FIELD OF THE INVENTION

The invention relates generally to liquid chromatography systems. More particularly, the invention relates to an apparatus that reduces the temperature variation among samples in a sample compartment of a liquid chromatography system.

BACKGROUND

A liquid chromatography system typically includes a sample compartment that provides a controlled environment for samples to be analyzed. The temperature within the sample compartment is ideally maintained at a constant value during measurements. For example, the sample compartment may be cooled to a temperature below the ambient temperature using thermoelectric cooling. One or more fans are used to generate an airflow that is directed across the cooling system and through the sample compartment. Structures within the sample compartment can interrupt or restrict the cooling airflow, thereby causing the air temperature within the compartment to vary with location. In some instances, the temperature variations within the compartment can cause unacceptable variations in the sample temperatures. A sample kept at the wrong temperature can degrade and influence the results of liquid chromatography analysis; therefore it is desirable to maintain each sample within a limited temperature range so that variation in sample temperatures does not significantly affect accuracy, repeatability, or sample integrity.

SUMMARY OF THE INVENTION

In one aspect, the invention features an apparatus for reducing a temperature variation of a liquid chromatography sample. The apparatus includes a sample tray to hold a plurality of samples and a tray drive configured to move the sample tray along a path inside a sample compartment of a liquid chromatography system. The apparatus also includes a sample needle to extract a sample from the sample tray and a needle drive to translate the sample needle. A control module is in electrical communication with the tray drive and the needle drive, and is used to control a position of the sample tray and a position of the sample needle during a sample load operation. The control module also controls a position of the sample tray along the path during a temperature averaging period.

In another aspect, the invention features an apparatus for reducing a temperature variation of a liquid chromatography sample. The apparatus includes a sample tray to hold a plurality of samples and a rotary drive configured to rotate the sample tray along a path inside a sample compartment of a liquid chromatography system. The apparatus also includes a sample needle to extract a sample from the sample tray and a needle drive to translate the sample needle. A control module in electrical communication with the rotary drive and the needle drive controls a translation of the sample needle and a rotation of the sample tray during a sample load operation. The control module controls a rotation of the sample tray during a temperature averaging period.

BRIEF DESCRIPTION OF THE DRAWINGS

The above and further advantages of this invention may be better understood by referring to the following description in conjunction with the accompanying drawings, in which like numerals indicate like structural elements and features in the various figures. For clarity, not every element may be labeled in every figure. The drawings are not necessarily to scale, emphasis instead being placed upon illustrating the principles of the invention.

DETAILED DESCRIPTION

In brief overview, the invention relates to an apparatus for reducing the variation of sample temperatures in a liquid chromatography system. A tray drive is used to move a sample tray inside a sample compartment of the liquid chromatography system. A control module coordinates the movement of the sample tray by the tray drive and the movement of a sample needle by a needle drive so that any sample in the sample tray can be injected into the mobile phase of the system during a sample load operation. The same tray drive is used to move the sample tray along a path during a temperature averaging period between injection times or at other times when sample loading does not occur. Differences in sample temperatures due to variations in the air temperature within the sample compartment are reduced, leading to more accurate and repeatable chromatographic measurement results.

Figure 1:
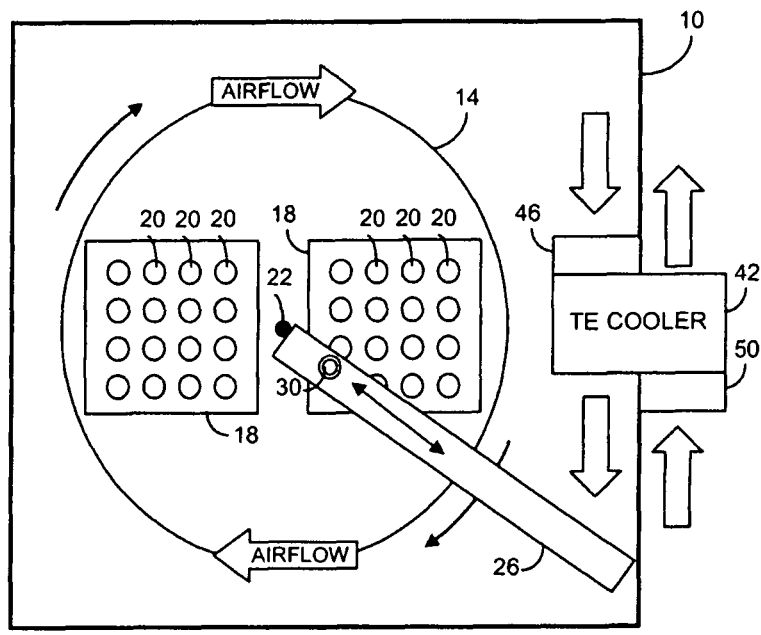
FIG. 1 is a block diagram illustrating a sample compartment for a liquid chromatography system.

FIG. 1 illustrates a portion of a liquid chromatography system according to an embodiment of the invention. The system includes a sample compartment 10. As used herein, a sample compartment means a substantially enclosed volume where a number of samples for chromatographic analysis are maintained in a thermally controlled environment. The sample compartment 10 includes a mounting platform 14 that holds two removable sample trays 18. In other embodiments a single sample tray or more than two trays are used. Each sample tray 18 has multiple sample vials or wells to hold a sample in a fixed position 20 with respect to the other samples in the sample tray 18. The sample tray 18 is secured to a rotary drive (not shown) so that rotation about a vertical axis 22 (i.e., normal to the plane of the figure) at a midpoint between the sample trays 18 is enabled. The rotary drive is used to change the angular position of the sample tray 18 and a needle drive 26 is used to change the position of a sample needle 30. Combined control of the needle drive 26 and rotary drive allows for the sample needle 30 to move to the location 20 of any sample and to extract the sample for injection into the mobile phase of the chromatography system.

Figure 2:
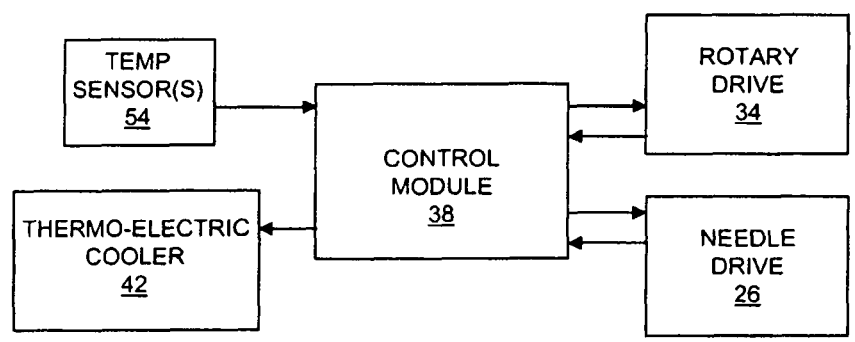
FIG. 2 is a block diagram showing a control system for coordinating a rotary drive and a needle drive for reducing the variation in sample temperatures for a liquid chromatography system according to an embodiment of the invention.

The rotary drive 34 and the needle drive 26 are managed by a control module 38 as shown in FIG. 2. In one embodiment, the control module 26 also controls a thermo-electric cooler 42 in response to the temperature sensed by one or more sensors 54 inside the sample compartment 10. The control module 38 coordinates operation of the rotary drive 34 and needle drive 26 so that the sample needle 30 moves to sample locations to extract samples for analysis in an automated manner.

Referring again to FIG. 1, the thermo-electric cooler 42 is mounted through a wall of the sample compartment 10. The thermoelectric cooler 42 can be a Peltier device or similar device adapted to cool the environment inside the compartment 10. One or more fans 46 mounted near the cooling surfaces of the cooler 42 are used to circulate cooled air throughout the sample compartment 10. An external fan 50 directs ambient air across external fins of the thermo-electric cooler 42 to remove excess heat.

Structures within the sample compartment 10 can interrupt or restrict the airflow thereby causing the internal air temperature to vary with location. Consequently, the sensed temperature may not accurately represent the temperature at each sample location 20.

The temperature of a sample can influence the results of the liquid chromatography analysis therefore it is desirable to maintain the temperature of each sample within a limited range so that repeatability of chromatographic results is improved. A maximum temperature difference $\Delta T$ between N samples can be specified for the system where $\Delta T$ is given by $$\Delta T = \max(T_s) - \min(T_s)$$

where each sample has a temperature $T_s$ (s=1 to N). By way of a particular example, the maximum temperature difference $\Delta T$ can be specified as 1° C.

Figure 3:
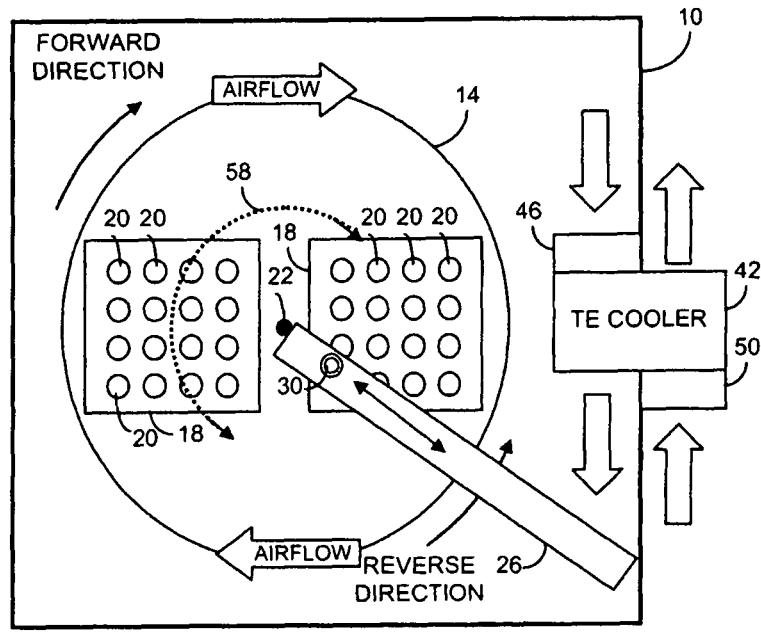
FIG. 3 is an illustration of an embodiment of an apparatus for reducing the variation in sample temperatures in a liquid chromatography system according to the invention.

The apparatus of the invention enables a reduction in the maximum temperature difference $\Delta T$ to be achieved. According to a preferred embodiment shown in FIG. 3, the mounting platform 14 is rotated about the vertical axis 22 so that the two sample trays 18 move along respective paths (only one path (dashed line) 58 shown for clarity) during a temperature averaging period when samples are not being extracted by the sample needle 30. The samples typically experience a range of air temperatures along the path 58 therefore the adverse affect of local temperature variations is diminished and the temperature of each sample approaches the average air temperature along its path of motion. In the illustrated embodiment, the mounting platform 14 is rotated over a portion of a circular path in a bidirectional manner. More specifically, the mounting platform 14 is rotated in a forward direction through 180° and then rotated in a reverse (opposite) direction through 180°. In other embodiments the rotation is unidirectional and/or the range of rotation is different. In one such embodiment the paths extend through 360°.

In one embodiment, the rate of rotation is set according to known temperature characteristics of the sample compartment 10 and the time available between the loadings of samples for injection.

The combination of rotational and translational motions can result in increased complexity during sample loading. Specifically, needle positioning errors based on angular error in rotational motion is compounded with increasing distance from the axis of rotation 22 whereas pure translational motion general results in placement errors ranges that do not vary with position. Thus the rotary drive 34 preferably includes a rotary encoder to ensure accurate angular positioning of the sample trays 18. By way of examples, the rotary encoder can be a magnetic rotary encoder or an optical rotary encoder as is known in the art.

Advantageously, the illustrated embodiment eliminates the added cost and size requirements that otherwise result from inclusion of a separate motion module to move the sample trays 18 to achieve sample temperature averaging. Rotation of the sample trays 18 does not disturb normal operation of the chromatography system because it occurs during temperature averaging periods that do not conflict with times when samples are extracted and loaded into the mobile phase. In one embodiment, after a loading operation is completed, the mounting platform 14 is returned to the path location immediately prior to the time the loading commenced. Alternatively, the mounting platform 14 can be moved to an initial path position after completion of a load operation.

Figure 4:
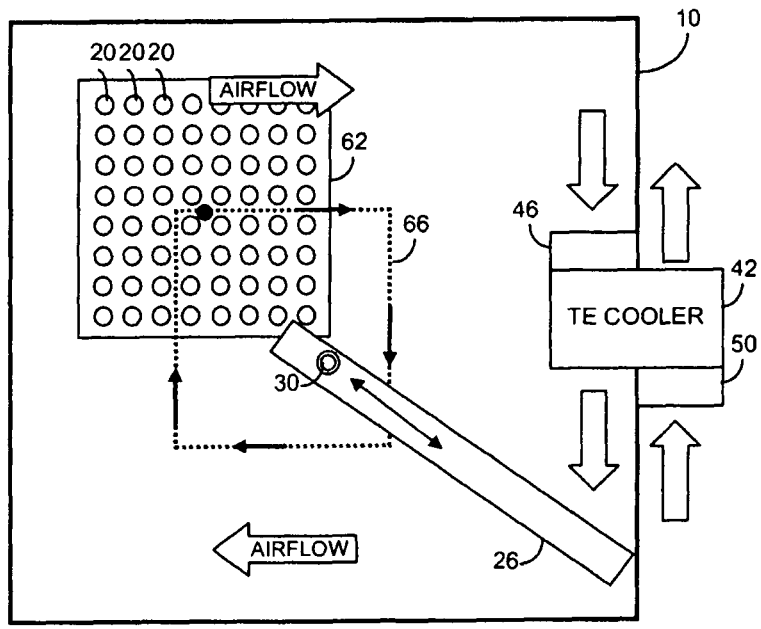
FIG. 4 is an illustration of another embodiment of an apparatus for reducing the variation in sample temperatures in a liquid chromatography system according to the invention.

In the embodiments described above, the path of an individual sample varies according to the distance of the sample from the axis of rotation 22. In some environments, it may be desirable to move all samples through a similar path length. FIG. 4 shows a sample compartment 10 with a single sample tray 62 having a high sample density. Each sample is moved along a rectangular path that is offset from the path 66 shown for the motion of the center of the sample tray 18. Although shown as a closed rectangular path, in other embodiments the path 66 can be of another form such as a linear path, a non-linear path, or a combination of linear and/or non-linear path segments. The path 66 can be predefined according to the space available inside the sample compartment 10 for moving the sample tray 62. The preferred path and the rate of motion along the path may be based on a known spatial temperature distribution within the sample compartment 10.

While the invention has been shown and described with reference to specific embodiments, it should be understood by those skilled in the art that various changes in form and detail may be made therein without departing from the spirit and scope of the invention as recited in the accompanying claims.

What is claimed is:

1. An apparatus for reducing a temperature variation of a liquid chromatography sample, comprising:
    a sample tray to hold a plurality of liquid chromatography samples;
    a tray drive configured to move the sample tray along a path inside a sample compartment of a liquid chromatography system;
    a sample needle to extract one of the liquid chromatography samples from the sample tray;
    a needle drive to translate the sample needle;
    a sample compartment having an enclosed volume that includes at least the sample tray and the sample needle, the enclosed volume being thermally controllable;
    a thermo-electric cooler disposed in the enclosed volume of the sample compartment; and
    a control module in electrical communication with the tray drive and the needle drive, the control module controlling a position of the sample tray and a position of the sample needle during a sample load operation, the control module controlling a position and rate of motion of the sample tray along the path during a temperature averaging period defined by the time available between the loadings of liquid chromatography samples for injection in the liquid chromatography system.

2. The apparatus of claim 1 wherein the position of the sample tray along the path during the temperature averaging period is unidirectional.

3. The apparatus of claim 1 wherein the position of the sample tray along the path during the temperature averaging period is bidirectional.

4. The apparatus of claim 1 wherein the control module controls a position of the sample tray along at least a portion of a circular path within the sample compartment during the temperature averaging period.

5. The apparatus of claim 1 wherein the sample tray is configured to hold the plurality of liquid chromatography samples in a two-dimensional array.

6. The apparatus of claim 1 further comprising a fan disposed in the enclosed volume of the sample compartment and configured to circulate air throughout the sample compartment.

7. An apparatus for reducing a temperature variation of a liquid chromatography sample, comprising:
   a sample tray to hold a plurality of liquid chromatography samples;
   a rotary drive configured to rotate the sample tray along a path inside a sample compartment of a liquid chromatography system;
   a sample needle to extract one of the liquid chromatography samples from the sample tray;
   a needle drive to translate the sample needle;
   a sample compartment having an enclosed volume that includes at least the sample tray and the sample needle, the enclosed volume being thermally controllable;
   a thermo-electric cooler disposed in the enclosed volume of the sample compartment; and
   a control module in electrical communication with the rotary drive and the needle drive, the control module controlling a translation of the sample needle and rotation of the sample tray during a sample load operation, the control module controlling a rotation and a rate of rotation of the sample tray during a temperature averaging period defined by the time available between the loadings of liquid chromatography samples for injection in the liquid chromatography system.

8. The apparatus of claim 7 wherein the rotation of the sample tray is bidirectional.

9. The apparatus of claim 7 wherein the rotation of the sample tray is unidirectional.

10. The apparatus of claim 7 wherein the path is a closed loop path.

11. The apparatus of claim 7 wherein the path is at least a portion of a circular path.

12. The apparatus of claim 7 wherein the sample tray comprises a pair of tray sections in diametric opposition, each of the sample trays configured to hold an array of liquid chromatography samples, wherein the sample tray is secured to the rotary drive for rotation about a midpoint between the tray sections.

13. The apparatus of claim 7 wherein the sample tray is configured to hold the plurality of liquid chromatography samples in a two-dimensional array.

14. The apparatus of claim 7 further comprising a fan disposed in the enclosed volume of the sample compartment and configured to circulate air throughout the sample compartment.

* * * * *